United States Patent [19]

Baker

[11] Patent Number: 5,514,130
[45] Date of Patent: May 7, 1996

[54] RF APPARATUS FOR CONTROLLED DEPTH ABLATION OF SOFT TISSUE

[75] Inventor: James Baker, Palo Alto, Calif.

[73] Assignee: Dorsal Med International, Menlo Park, Calif.

[21] Appl. No.: 320,304

[22] Filed: Oct. 11, 1994

[51] Int. Cl.⁶ .................................................. A61B 17/39
[52] U.S. Cl. ................................. 606/41; 606/48; 606/50
[58] Field of Search .................................. 606/41, 46, 48, 606/50; 607/98, 99, 113, 116

[56] References Cited

U.S. PATENT DOCUMENTS

| | | |
|---|---|---|
| 4,326,529 | 4/1982 | Doss et al. . |
| 4,362,160 | 12/1982 | Hiltebrandt . |
| 4,381,007 | 4/1983 | Doss . |
| 4,483,338 | 11/1984 | Bloom et al. . |
| 4,517,965 | 5/1985 | Ellison . |
| 4,593,691 | 6/1986 | Lindstrom et al. . |
| 4,811,733 | 3/1989 | Borsanyi et al. . |
| 4,873,976 | 10/1989 | Schreiber . |
| 4,895,148 | 1/1990 | Bays et al. . |
| 4,907,585 | 3/1990 | Schachar . |
| 4,924,865 | 5/1990 | Bays et al. . |
| 4,966,597 | 10/1990 | Cosman ................................. 606/50 |
| 4,976,715 | 12/1990 | Bays et al. . |
| 5,334,193 | 8/1994 | Nardella ................................. 606/41 |
| 5,458,596 | 10/1995 | Lax et al. ................................. 606/41 |

*Primary Examiner*—Lee S. Cohen
*Attorney, Agent, or Firm*—Haynes & Davis

[57] ABSTRACT

An RF ablation apparatus has a delivery catheter with a delivery catheter lumen and a delivery catheter distal end. A first RF electrode is positioned in the delivery catheter lumen. The first RF electrode has a distal end, RF conductive surface, and a lumen. A second RF electrode has a distal end. The second RF electrode is at least partially positioned in the lumen of the first catheter, with its distal end positioned at the exterior of the first RF electrode distal end. Additionally, the second RF electrode distal end has a geometry that permits it to be substantially a groundpad. The distal end of the first RF electrode is moved in a direction away from the second RF electrode distal end to create a painting effect of an ablation band or line between the two distal ends. Alternatively, the distal end of the second RF electrode can be moved in a direction away from the distal end of the first RF electrode. An RF insulative sleeve or coating is placed or positioned along a second RF electrode conductive surface where it is substantially adjacent to the first electrode conductive surface. An RF power source is coupled to the first and second RF electrodes.

44 Claims, 14 Drawing Sheets

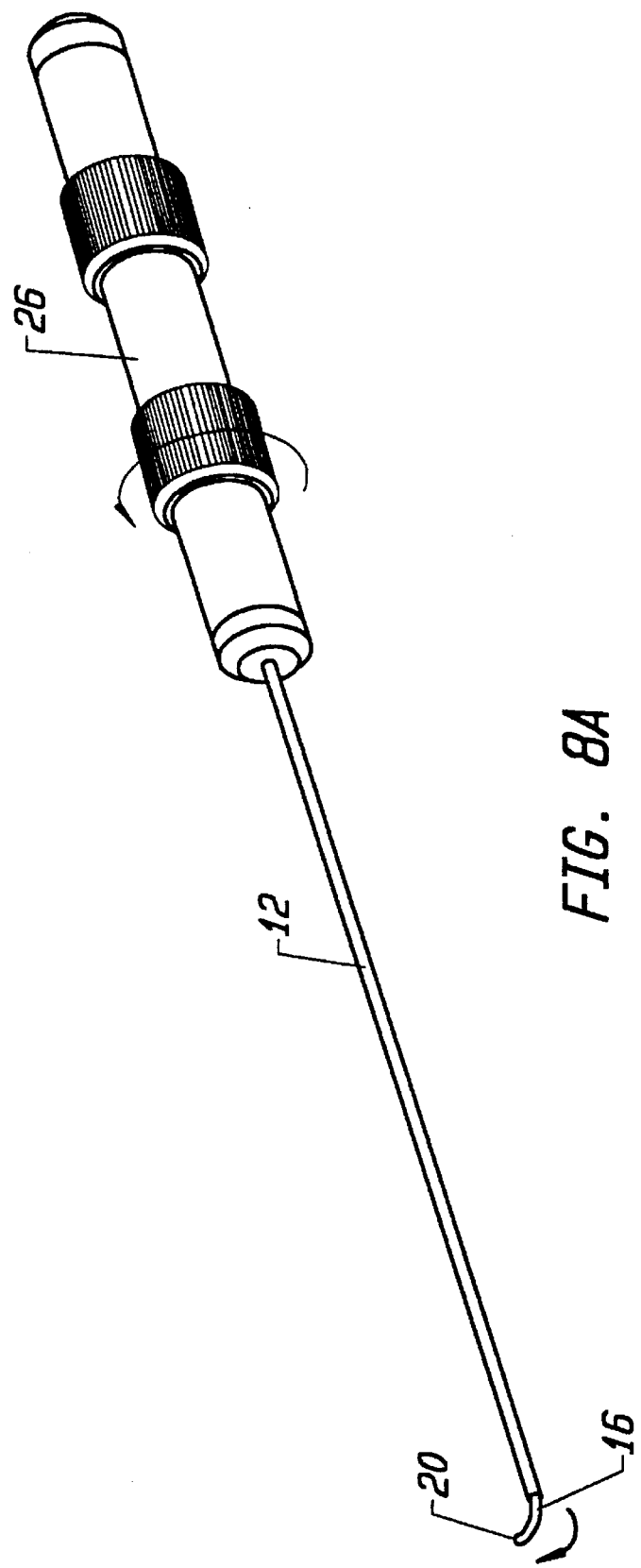

RF APPARATUS FOR CONTROLLED DEPTH ABLATION OF SOFT TISSUE

BACKGROUND OF THE INVENTION

1. Field of the Invention

This invention relates generally to an RF apparatus and the controlled contraction of soft tissue, and more particularly, to an RF apparatus that paints a line of ablation to achieve controlled contraction of soft tissue.

2. Description of the Related Art

Instability of peripheral joints has long been recognized as a significant cause of disability and functional limitation in patients who are active in their daily activities, work or sports. Diarthrodial joints of the musculoskeletal system have varying degrees of intrinsic stability based on joint geometry and ligament and soft tissue investment. Diarthrodial joints are comprised of the articulation of the ends of bones and their covering of hyaline cartilage surrounded by a soft tissue joint capsule that maintains the constant contact of the cartilage surfaces. This joint capsule also maintains, within the joint, the synovial fluid that provides nutrition and lubrication of the joint surfaces. Ligaments are soft tissue condensations in or around the joint capsule that reinforce and hold the joint together while also controlling and restricting various movements of the joints. Ligaments, joint capsule, and connective tissue are largely comprised of collagen.

When a joint becomes unstable, its soft tissue or bony structures allow for excessive motion of the joint surfaces relative to each other, and in direction not normally permitted by the ligaments or capsule. When one surface of a joint slides out of position relative to the other surface, but some contact remains, subluxation occurs. When one surface of the joint completely disengages and losses contact with the opposing surface, a dislocation occurs. Typically, the more motion a joint normally demonstrates, the more inherently loose the soft tissue investment is surrounding the joint. This makes some joints more prone to instability than others. The shoulder, glenohumeral joint, for example, has the greatest range of motion of all peripheral joints. It has long been recognized as having the highest subluxation and dislocation rate because of its inherent laxity relative to more constrained "ball and socket" joints such as the hip.

Instability of the shoulder can occur congenitally, developmentally, or traumatically and often becomes recurrent, necessitating surgical repair. In fact, subluxations and dislocations are a common occurrence and cause for a large number of orthopedic procedures each year. Symptoms include pain, instability, weakness and limitation of function. If the instability is severe and recurrent, functional incapacity and arthritis may result. Surgical attempts are directed toward tightening the soft tissue restraints that have become pathologically loose. These procedures are typically performed through open surgical approaches that often require hospitalization and prolonged rehabilitation programs.

More recently, endoscope (arthroscopic) techniques for achieving these same goals have been explored with variable success. Endoscopic techniques have the advantage of being performed through smaller incisions, and therefore are usually less painful. Such techniques are performed on an outpatient basis, associated with less blood loss and lower risk of infection and have a more cosmetically acceptable scar. Recovery is often faster postoperatively than using open techniques. However, it is often more technically demanding to advance and tighten capsule or ligamentous tissue arthroscopically because of the difficult access to pathologically loose tissue, and because it is very hard to determine how much tightening or advancement of the lax tissue is clinically necessary. In addition, fixation of advanced or tightened soft tissue is more difficult arthroscopically than through open surgical methods.

Collagen connective tissue is ubiquitous in the human body and demonstrates several unique characteristics not found in other tissues. It provides the cohesiveness of the musculoskeletal system, the structural integrity of the viscera as well as the elasticity of integument. There are basically five types of collagen molecules, with Type I being most common in bone, tendon, skin and other connective tissues, and Type III is common in muscular and elastic tissues.

Intermolecular cross links provide collagen connective tissue with unique physical properties of high tensile strength and substantial elasticity. A previously recognized property of collagen is hydrothermal shrinkage of collagen fibers when elevated in temperature. This unique molecular response to temperature elevation is the result of rupture of the collagen stabilizing cross links and immediate contraction of the collagen fibers to about one-third of their original lineal distention. Additionally, the caliber of the individual fibers increases greatly, over four fold, without changing the structural integrity of the connective tissue.

There has been discussion in the existing literature regarding alteration of collagen connective tissue in different parts of the body. One known technique for effective use of this knowledge of the properties of collagen is through the use of infrared laser energy to effect tissue heating. The importance in controlling the localization, timing and intensity of laser energy delivery is recognized as paramount in providing the desired soft tissue shrinkage effects without creating excessive damage to the surrounding non-target tissues.

Shrinkage of collagen tissue is important in many applications. One application is the shoulder capsule. The capsule of the shoulder consists of a synovial lining and three well defined layers of collagen. The fibers of the inner and outer layers extend in a coronal access from the glenoid to the humerus. The middle layer of the collagen extends in a sagittal direction, crossing the fibers of the other two layers. The relative thickness and degree of intermingling of collagen fibers of the three layers vary with different portions of the capsule. The ligamentous components of the capsule are represented by abrupt thickenings of the inner layer with a significant increase in well organized coarse collagen bundles in the coronal plane.

The capsule functions as a hammock-like sling to support the humeral head. In pathologic states of recurrent traumatic or developmental instability this capsule or pouch becomes attenuated, and the capsule capacity increases secondary to capsule redundance.

In cases of congenital or developmental multi-directional laxity, an altered ratio of Type I to Type III collagen fibers may be noted. In these shoulder capsules, a higher ratio of more elastic type III collagen has been described.

There exists a need for an apparatus to effect controlled ablation of soft tissue along a painted band or line created by the introduction of RF energy. It would be desirable to provide an RF ablation apparatus which can provide controlled ablation depth of soft tissue to shrink the tissue to a desired state along a selectable surface, including but not limited to a narrow line.

SUMMARY OF THE INVENTION

It is an object of the present invention to provide an RF ablation apparatus which creates controlled delivery of RF energy to a desired tissue site. Another object of the present invention is to provide an RF ablation apparatus which paints a band or line of ablation along a selected tissue site.

A further object of the present invention is to provide an RF ablation apparatus which includes a first RF electrode and a second RF electrode, with the first RF electrode being movable along an elongated portion of the second RF electrode to create a painting ablation of a selected tissue site.

A further object of the present invention is to provide an RF ablation apparatus which provides selectable painting ablation of soft tissue.

Another object of the present invention is to provide an RF ablation apparatus which includes two RF electrodes, with one being slideable along the other to create a painting ablation effect that can be repeated any number of times to achieve a desired level of tissue ablation.

A further object of the present invention is to provide an RF ablation apparatus which includes two RF electrodes which have distal ends that are positioned laterally in relation to a distal end of an associated delivery catheter.

Yet another object of the present invention is to provide an RF ablation apparatus which includes two RF electrodes with distal ends, one of the RF electrode distal ends having a geometry and size sufficient to make it substantially a ground pad.

Another object of the present invention is to provide an RF ablation apparatus with two RF electrodes with distal ends, and one of the distal ends is radiused with substantially no sharp edges.

A further object of the present invention is to provide an RF ablation apparatus with two RF electrodes with distal ends, and one of the distal ends has an RF conduction region that has a sharp edge.

Yet another object of the present invention is to provide an RF ablation apparatus which provides continuous, adjustable ablation of soft tissue.

A further object of the present invention is to provide an RF ablation apparatus which provides for the maximum amount of collagen contraction without dissociation of the collagen structure.

Yet another object of the present invention is to provide an RF ablation apparatus to deliver a controlled amount of RF energy to collagen soft tissue of a joint in order to contract and restrict the soft tissue elasticity and improve joint stability.

These and other objects of the invention are obtained with an RF ablation apparatus including, a delivery catheter, a delivery catheter lumen, and a delivery catheter distal end. A first RF electrode is positioned in the delivery catheter lumen. The first RF electrode has a first RF electrode distal end, a first RF electrode conductive surface, and a first RF electrode lumen. A second RF electrode, with a second RF electrode distal end, is at least partially positioned in the first RF electrode lumen. The second RF electrode distal end has a geometry that permits it to act substantially as groundpad. The first RF electrode is moved away from the second RF electrode distal end, creating an ablation band or line between the distal ends of the two electrodes. An RF insulative sleeve is positioned along a second RF electrode conductive surface that is substantially adjacent to the first RF electrode conductive surface. An RF power source is coupled to the first and second RF electrodes.

In another embodiment of the present invention, the RF ablation apparatus includes a delivery catheter with a delivery catheter lumen. A first RF electrode is positioned in the delivery catheter lumen. The first RF electrode has a first RF electrode distal end with an RF conductive surface, and a first RF electrode lumen. A second RF electrode has an elongated body that terminates at a second RF electrode distal end with an RF conductive surface. The second RF electrode distal end has a diameter that is larger than the elongated body. The second RF electrode is at least partially positioned in the first RF electrode lumen, with the second RF electrode distal end positioned at the exterior of the first RF electrode distal end. An ablation band or line is created between the two distal ends of the electrodes as the first RF electrode is moved in a direction away from the second RF electrode distal end.

The second electrode distal end is radiused, and has substantially no sharp edges. A portion of the second electrode distal end can be partially covered with an RF insulator. The first electrode distal end has a sharp edge. Either one or both of the first and second electrode distal ends can be deployed in a lateral direction relative to a longitudinal axis of the delivery catheter, permitting ablation in difficult to access areas, such as around hard objects.

Significantly, the first RF electrode distal end is movable in a direction away from the second RF electrode distal end. This creates a band of ablation. The size of the band is dependent of the relative sizes of the distal ends of the two electrodes. The depth of the ablation is determined by the speed at which the first RF electrode distal end is moved away from the second RF electrode distal end, as well as the number of passes the first RF electrode distal end makes along the ablation band. These two parameters provide for continuous adjustable ablation to the selected tissue site.

The width of the ablation band is determined by the width of the first electrode distal end. Suitable sizes depend on the application and specific tissue site.

Either one or both distal ends of the two electrodes can be deployed in a lateral direction relative to the delivery catheter. This is achieved through a variety of mechanisms including but not limited to, (i) a pull wire can be attached to the distal ends, (ii) the distal ends can be formed of a shaped memory metal, (iii) substantially all of the first and second RF electrodes can be formed of a shaped memory metal, (iv) each electrode can include a resistive wire which, when heated, causes the distal end of the respective electrode to be laterally deployed and (v) the distal ends of the first RF electrode and the delivery catheter can be formed in a lateral direction relative to the longitudinal axis of the delivery catheter.

Movement of the first RF electrode distal end can occur in a number of ways. The first RF electrode can be attached to the delivery catheter. As the delivery catheter is moved away from the second RF electrode distal end, the first RF electrode distal end is also moved, delivering RF ablation energy in a painting-like manner. Additionally, the first RF electrode can be slidably received in the lumen of the delivery catheter. In this embodiment, the first RF electrode is moved away from the second electrode distal end independently of movement of the delivery catheter. The same painting effect is achieved.

Portions of either one or both of the first and second electrode distal ends can be partially covered with an RF insulator. This further defines the size of the ablation band.

Optionally included with the ablation apparatus of the present invention is a feedback device in response to a detected characteristic of all or a portion segment of the ablation band that provides a controlled delivery of RF energy to the first and second electrodes. The detected characteristic can be an impedance at a section of ablation band, a temperature profile of the ablation band, and the like.

The first RF electrode distal end can be rotated as it is moved in a direction away from the second RF electrode distal end, creating a multi-radiused ablation band. The first RF electrode distal end can be moved any number of times away from the second RF electrode distal end in a painting like manner.

DESCRIPTION OF THE DRAWINGS

FIG. 8(a) is a perspective view of the RF ablation device, with both electrodes extended laterally relative to the delivery catheter.

DETAILED DESCRIPTION OF THE PREFERRED EMBODIMENTS

The present invention is an RF ablation apparatus that includes first and second RF electrodes, a delivery catheter and an RF energy source. The first RF electrode is positioned in a lumen of the delivery catheter. It has a distal end that extends beyond a distal end of the delivery catheter. The second RF electrode is positioned in a lumen of the first RF electrode, and has a geometry that permits it to be substantially a groundpad. It has a distal end that extends beyond the distal end of the first RF electrode distal end. As the first RF electrode is moved in a direction away from the second RF electrode, an ablation band is created between the second and first RF electrode distal ends. The first RF electrode can be moved any number of times along the ablation band in order to ablate more tissue. The ablation apparatus is particularly suitable for creating well defined ablation bands, of substantially even depth, along a tissue site, even in difficult to access tissue sites such as peripheral joints. Movement of the second RF electrode creates a painting of RF energy along a tissue site. Again, the second RF electrode can be moved along the ablation band any number of times to provide numerous painting applications of RF energy. The present invention provides for the continuous adjustable ablation. The lesion created by the ablation is a painted line or band along the tissue. Depth control of ablation is controlled with speed of movement of the two distal ends of the electrodes away from each other. Additionally, continuous ablation can be achieved.

Figure 1:
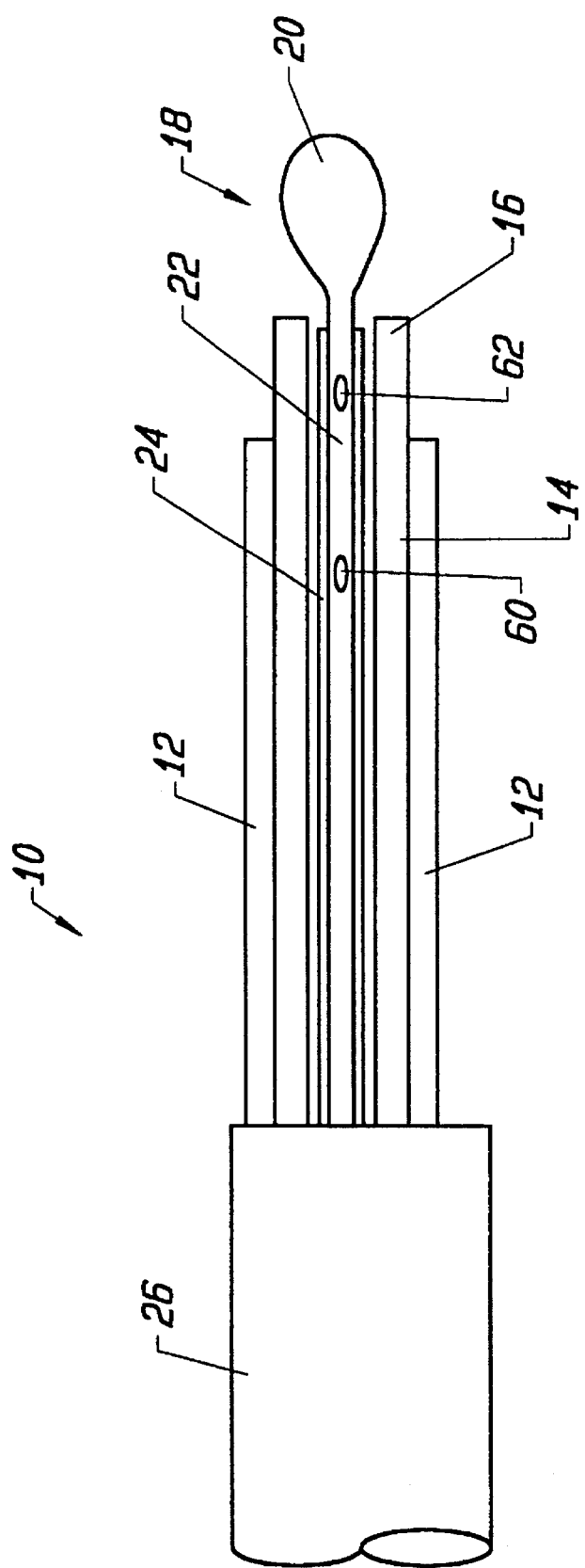
FIG. 1 is a cross-sectional view of the ablation apparatus of the present invention.

Referring now to FIG. 1, ablation apparatus 10 includes a delivery catheter 12, first RF electrode 14 with a distal end 16, second RF electrode 18 with a distal end 20 and an elongated body 22, and a sleeve of RF insulation 24 positioned along substantially the entire length of elongated body 22. A handpiece 26 is associated with delivery catheter 12. Insulation sleeve 24 can extend along only a desired portion of elongated body 22, and can also cover a portion of second RF electrode distal end 20. In one embodiment of the invention, the sizes of delivery catheter 12, first RF electrode 14, first RF electrode distal end 16, second RF electrode distal end 20, and elongated body are in the range of about 0.5 to 10 mm respectively.

Delivery catheter 12, first RF electrode 14 and second RF electrode 18 can be made of gold, aluminum, tungsten, nickel titanium, platinum, stainless, copper and brass.

The geometry and dimensions of second RF electrode distal end 20 are selected so that it serves as a groundpad in a bipolar mode of operation. Additionally, it may be preferred that second RF electrode distal end 20 have a wider width than the width of elongated body 22.

Figure 2:
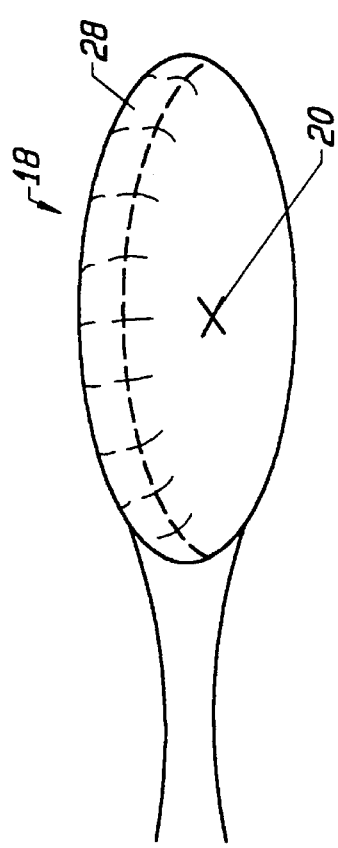
FIG. 2 is a perspective view of the second RF electrode distal end, illustrating in this embodiment that the distal end has radiused edges.
Figure 4:
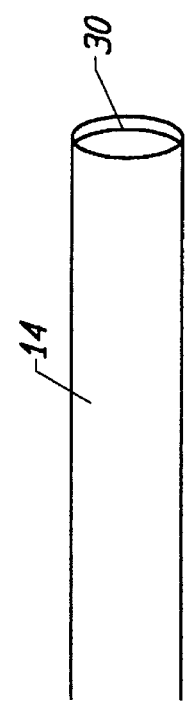
FIG. 4 is a perspective view of a cylindrical first RF electrode with a sharp edge distal end.
Figure 3:
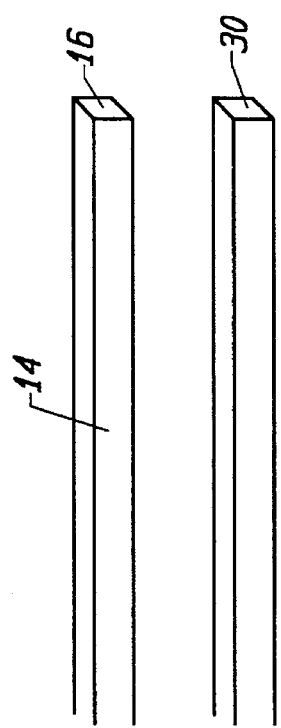
FIG. 3 is a perspective view of one embodiment of the first RF electrode distal end with sharp edges.

First RF electrode 14 is moved in a direction away from second RF electrode 18, as more fully described later in this disclosure. Further, second RF electrode 18 can be moved in a direction away from first RF electrode 14. This creates a painting-type of affect, applying RF ablative energy to a selected tissue site to create an ablation band. This is achieved by the bipolar ablation occurring between distal ends 16 and 20, with second RF electrode distal end 20 serving as a groundpad. To achieve this result, it is desirable if second RF electrode distal end 20 have no sharp edges, and that the edges 28 are radiused, as illustrated in FIG. 2. Further, all or a portion of first electrode distal edge 30 should be a sharp edge, as shown in FIG. 3. FIG. 4 illustrates an embodiment of first RF electrode 14 with a substantially cylindrical geometry. It also has a sharp edge 30.

Figure 5:
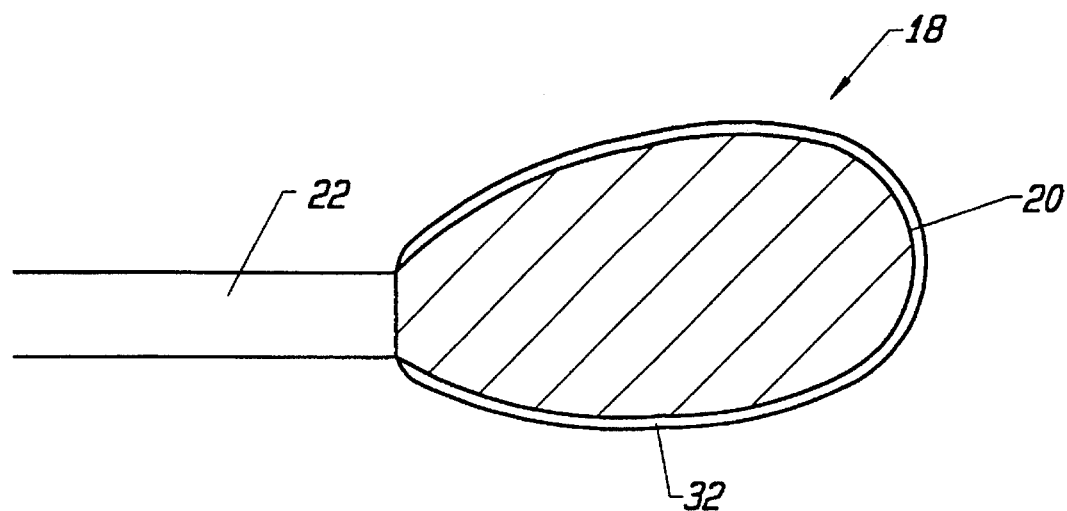
FIG. 5 is a perspective view of the second RF electrode, including a generally elongated section of the electrode. An RF insulative coating is on one side of the electrode distal end.
Figure 6:
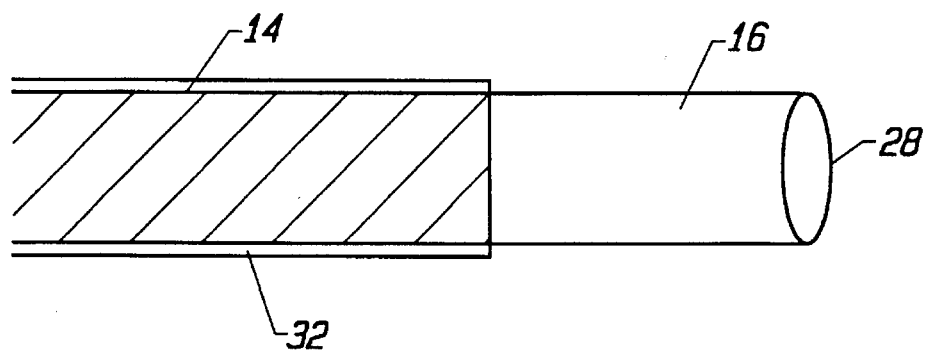
FIG. 6 is a perspective view of the first RF electrode, with a portion of the electrode covered by an RF insulative coating.

Referring now to FIGS. 5 and 6, portions of RF electrodes 14 and 18 can include an RF insulator 32 positioned on a portion of distal ends 16 and 20. RF insulator 32 can, for example, be deposited on only one side of distal ends 16 and 20 so that there is an RF conductive surface on only one side of a distal end.

Figure 7:
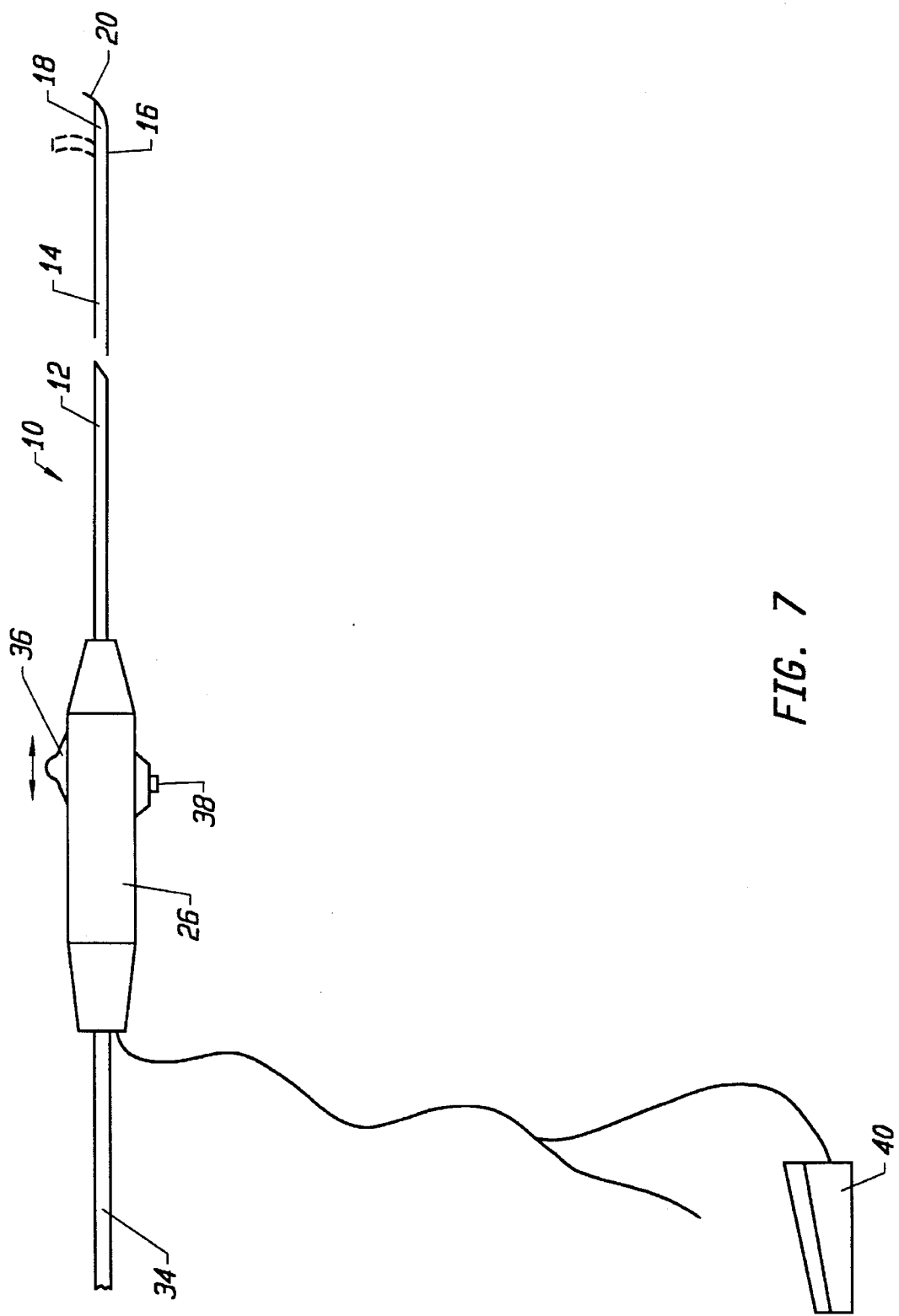
FIG. 7 is a perspective view of the ablation apparatus of the invention, including a handle associated with the delivery catheter, electrical connectors, and a foot switch to activate the RF energy source.

As illustrated in FIG. 7, delivery catheter 12 attaches to handle 26. Electrical cables 34 are coupled to first RF electrode 14, second RF electrode 18 and to an RF energy source (not shown). A first actuator 36 deploys movement of first electrode 14 in and out of delivery catheter 12. This causes first electrode distal end 16 to move in a direction to and from second electrode distal end 20. First actuator 36 can also deploy the movement of delivery catheter 12. Alternatively, first activator can deploy movement of delivery catheter 12. When first electrode 14 is fixably positioned in the lumen of delivery catheter 12, the movement of first electrode 14, relative to the position of second electrode distal end 20, is determined by the slideable movement of delivery catheter 12 relative to second electrode distal end 20. A suitable method of fixably positioning first electrode 14 in delivery catheter is by attachment to handle 26. In either case, first electrode distal end 16 is moved in a direction away from second electrode distal end 20, one or more times, to create an RF energy painting effect on the tissue, resulting in controlled shrinkage of the tissue, and collagen fibers without disrupting the structure of the collagen. Controlled, even ablation is achieved along a narrow band of a desired size. Suitable sizes of the band are about 0.5 to 10 mm.

A second actuator 38 is associated with pull wires that attach to distal ends 16 and 20, or to other sections of first and second electrodes 14 and 18 respectively. When tension is applied to the pull wires this causes distal ends 16 and 20 to deflect in a lateral direction relative to a longitudinal axis of delivery catheter 12. A foot switch is coupled to the electrical cables associated with handle 26 and it activates the RF power source.

Figure 8B:
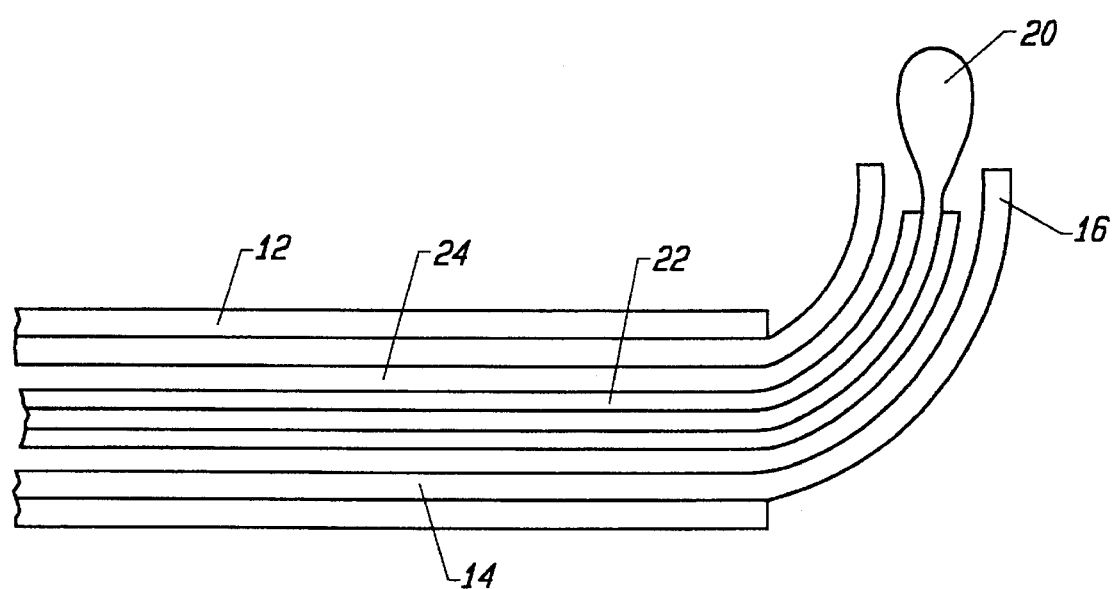
FIG. 8(b) is a cross-sectional view of the RF ablation device, with both electrodes extended laterally relative to the delivery catheter.

FIGS. 8(*a*) and 8(*b*) more fully illustrate the lateral deflection, and flexibility of first RF electrode 14 and second RF electrode 18. Electrodes 14 and 18 can be deflected by a variety of mechanisms including, (i) electrodes 14 and 18, or distal ends 16 and 20, can be made of a shaped memory metal, such as NiTi, commercially available from RayChem Corporation, Menlo Park, Calif., (ii) the use of pull wires or other similar devices, (iii) inclusion of a resistive wire in one or both of electrodes 14 and 18 and (iv) inclusive of a heated fluid in one or both of electrodes 14 and 18 that are formed of a deformable material at elevated temperatures.

Lateral deflection of RF electrodes 14 and 18 is shown in FIG. 8 out of the distal end of delivery catheter 12. RF electrodes 14 and 18 can be deployed up to 7 cm or greater. Additionally, RF electrodes 14 and 18 can be laterally deployed up to about 90 degrees or greater. RF electrodes 14 and 18 can be deployed sufficiently to reach around difficult to access areas such as discs of the spine, and around surfaces of peripheral joints.

Figure 9:
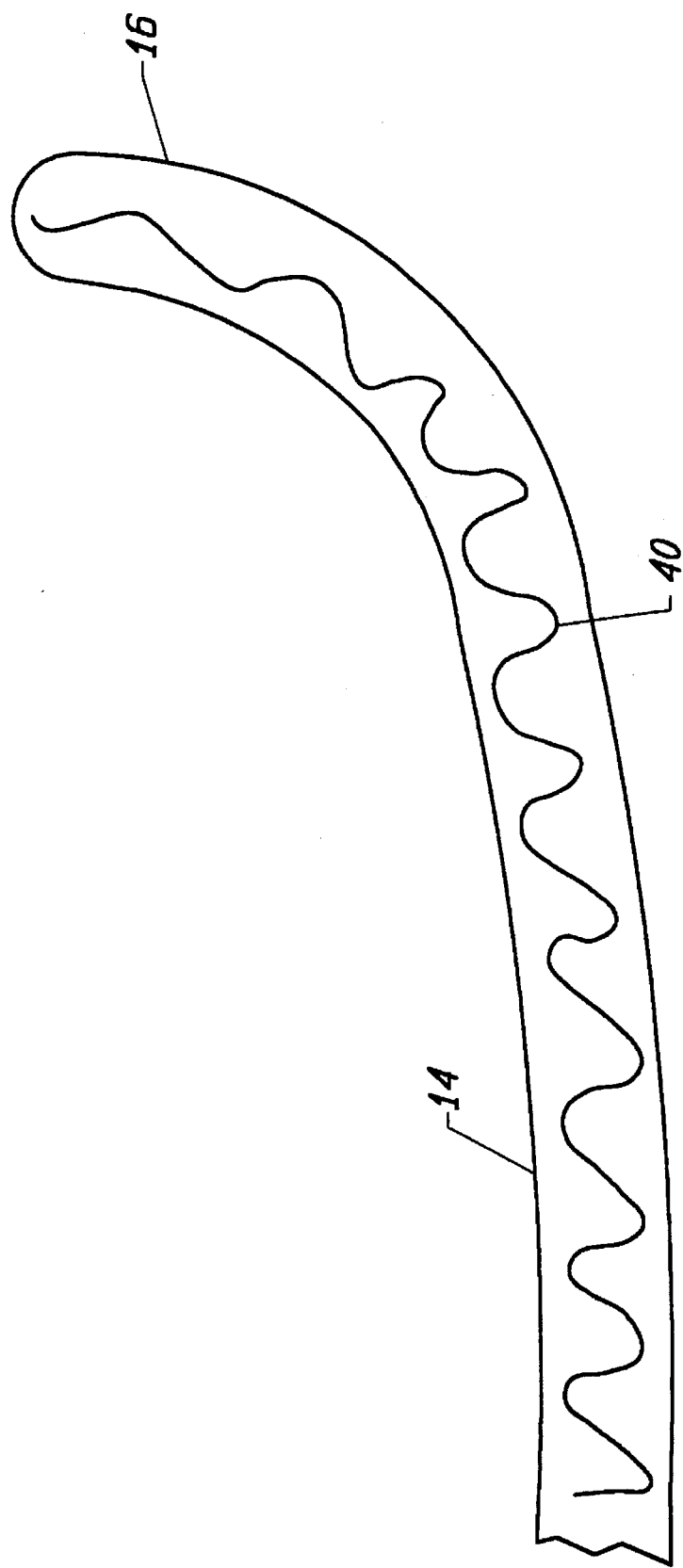
FIG. 9 is a cross-sectional view of the second RF electrode, including a resistive heating wire disposed in the lumen of the electrode.

As previously mentioned, one method of laterally deploying RF electrodes 14 and 18 is with the use of a resistive wire 40, illustrated in FIG. 9. Resistive wire may be placed in one or both of RF electrodes 14 and 18. Application of current, from a suitable current source, causes deflection. The extent of the deflection is dependent on the type of wire used, the amount of resistive wire 40 at any location, and the amount of current applied. Preferably, the greatest amount of resistive wire 40 is at distal ends 16 and 20.

Figure 10:
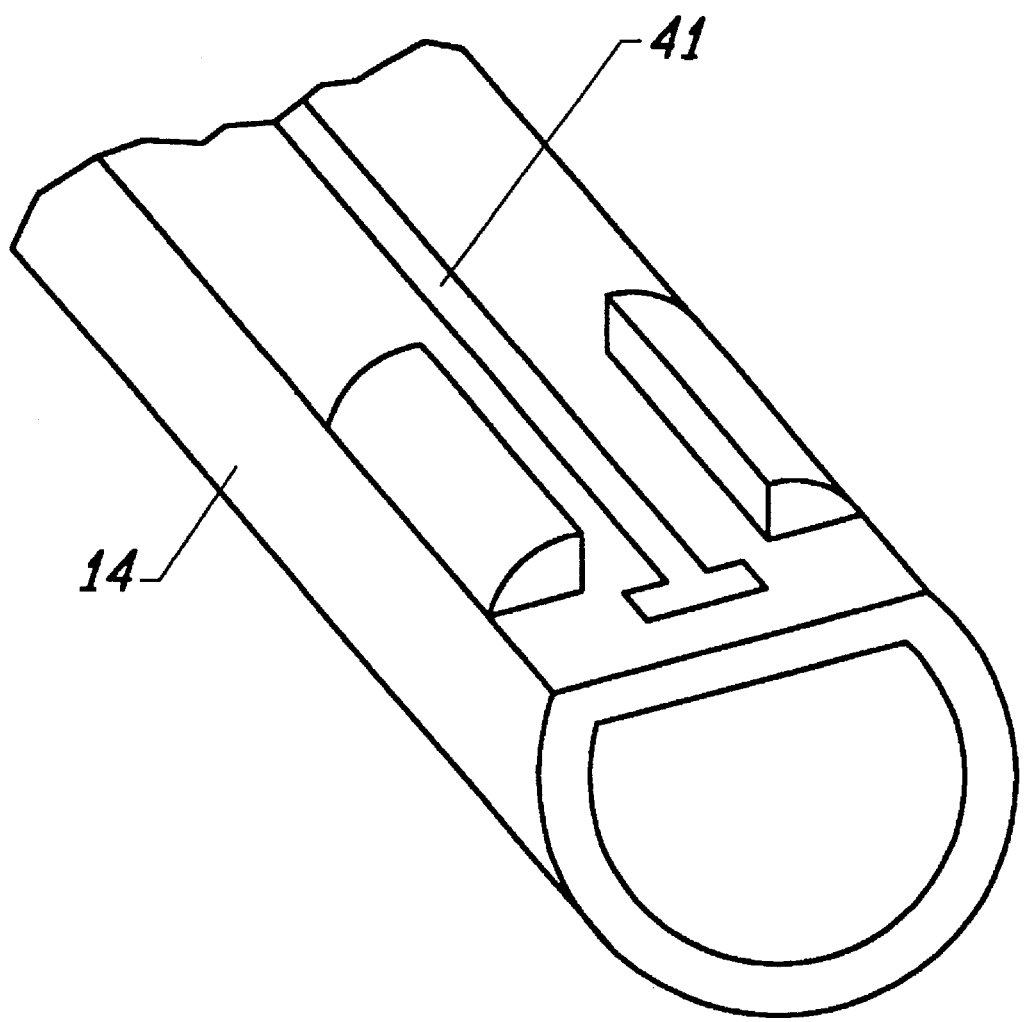
FIG. 10 is a perspective view of the first RF electrode, including a pull wire attached to the outer surface of the electrode.

As shown in FIG. 10, pull wire 41 can attach to a flat formed on the exterior of RF electrode 14. However, RF electrode 14 need not have a flat surface formed at its exterior. Additionally, pull wire 41 can attach to the interior of RF electrode 14. Pull wire 41 can similarly be attached to RF electrode 18. Wire EDM technology can be used to form the flat on RF electrode 14. Pull wire 41 need not be an actual wire. It can also be a high tensile strength cord, such as Kevlar. Pull wire 41 can be made of stainless steel flat wire, sheet material, and the like.

Figure 11:
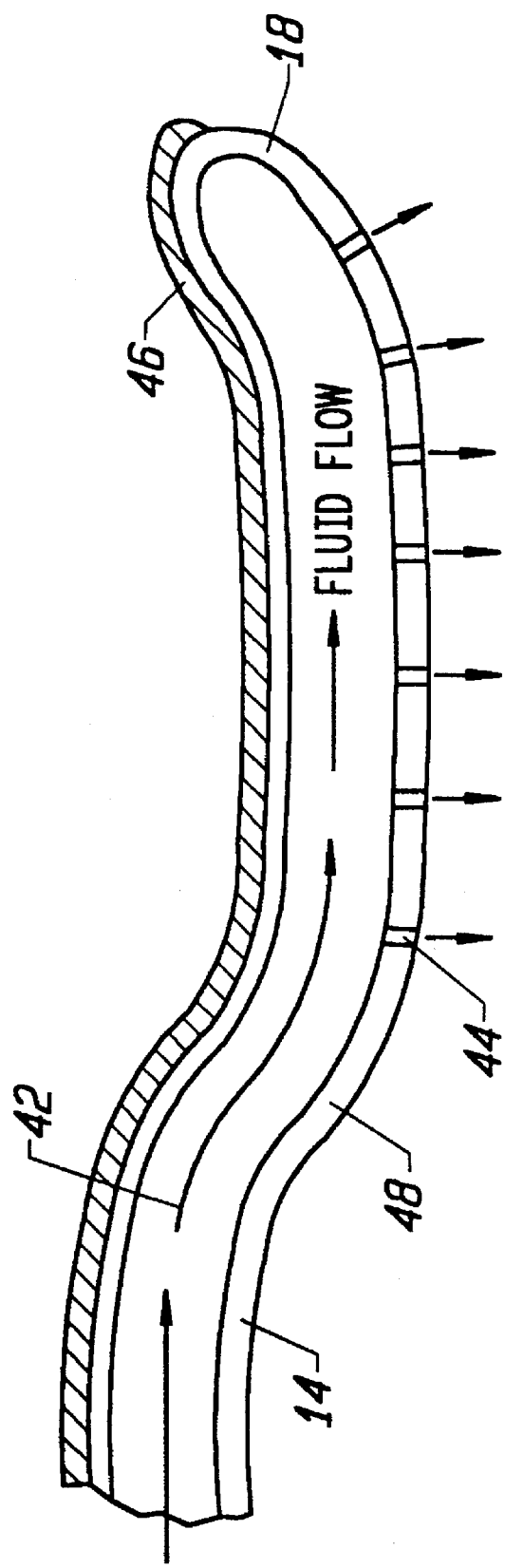
FIG. 11 is a cross-sectional view of the first RF electrode, including an RF insulator placed on the back surface of the electrode, and electrolytic solution passing through the lumen of the electrode which is then passed through an RF conductive surface to a selected tissue site.

As shown in FIG. 11, an electrolytic solution or gel 42 can be introduced through the lumen of first RF electrode 14 and delivered to the selected ablation tissue site through fluid distribution ports 44 formed in first electrode 14. In one embodiment, one side of first RF electrode 14 is coated with an RF insulator 46, so that only the opposite side provides an RF energy conductive surface 48. It will appreciated that second RF electrode 18 can also include electrolytic solution or gel 42 in a similar manner, as described above with first RF electrode 14.

Figure 12:
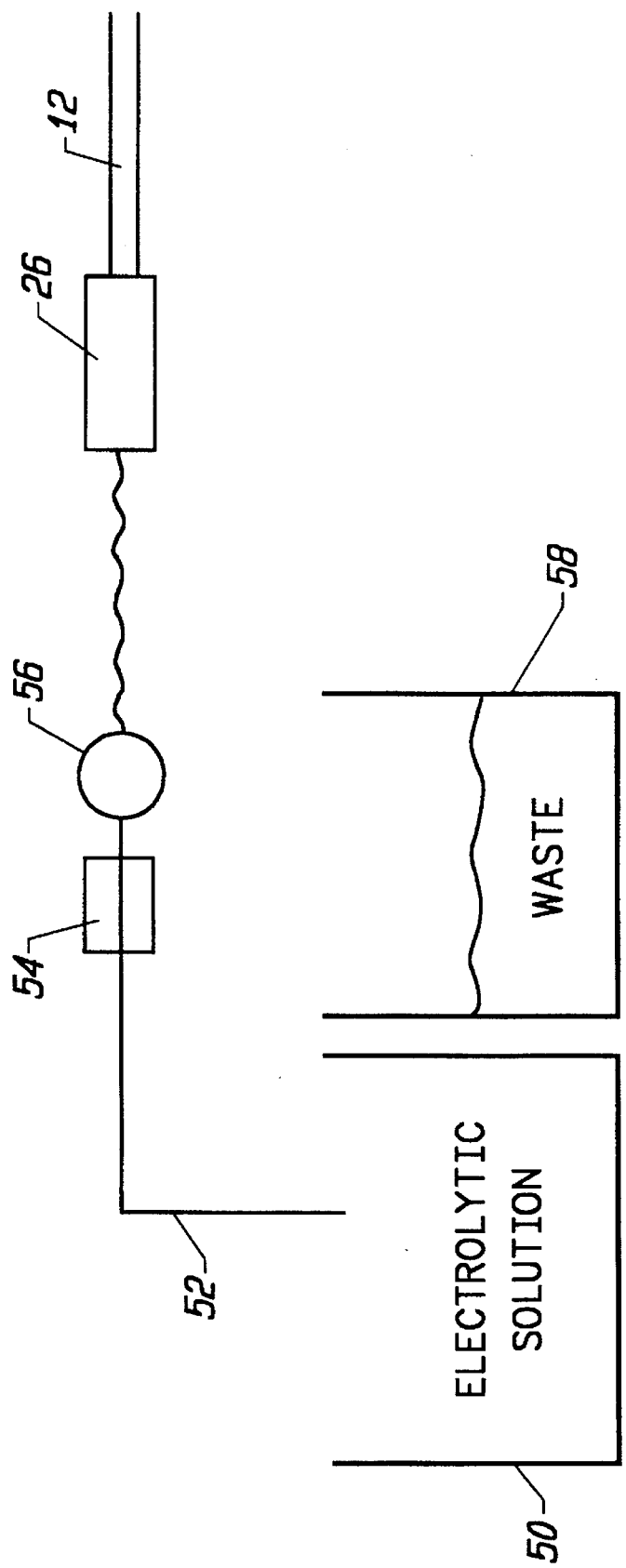
FIG. 12 is a block diagram of a system for delivering electrolytic solution to a selected tissue site through the second RF electrode.

Referring now to FIG. 12, electrolytic solution or gel 42 is in a holding container 50, and transferred through a fluid conduit 52 to a temperature controller 54 which can cool and heat electrolytic solution or gel 42 to a desired temperature. A pump 56 is associated with fluid conduit 52 to transfer fluid through the system and delivers electrolytic solution or gel 42 to handpiece 26 to first and second RF electrodes 14 and 18. Returning electrolytic solution or gel 42 is passed to a waste container 58. The flow rate of electrolytic solution 42 can be in the range of less than about 1 cc/min. to greater than 5 cc/min.

Ablation apparatus 10 provides a method of painting a thin band of ablation along the surface of a body structure, including but not limited to soft tissue. It also provides for the controlled contraction of collagen soft tissue. The collagen soft tissue is contracted to a desired shrinkage level without dissociation and breakdown of the collagen structure. It can be used in the shoulder, spine, for cosmetic applications, and the like. It will be appreciated to those skilled in the art that ablation apparatus 10 has a variety of different applications, not those merely specifically mentioned in this specification. Some specific applications include joint capsules, such as the gleno-humoral joint capsule of the shoulder, herniated discs, the meniscus of the knee, in the bowel, for hiatal hernias, abdominal hernias, bladder suspensions, tissue welding, DRS. and the like.

Ablation apparatus 10 delivers RF energy and thermal energy to soft tissue such as collagen soft tissue. First RF electrode 14 is painted across the collagen soft tissue sequentially until the maximum shrinkage occurs. In one embodiment, the collagen soft tissue is contracted in an amount of about two-thirds of its resting weight. A temperature range of about 43 to 90 degrees C. is preferred. More preferred, the temperature range is about 43 to 75 degrees C. Still more preferred is a temperature range of about 45 to 60 degrees C.

In one specific embodiment of the invention, joint capsules are treated to eliminate capsular redundance. More specifically, ablation apparatus 10 is utilized to contract soft collagen tissue in the gleno-humoral joint capsule of the shoulder.

Ablation apparatus 10 provides an ablation band or line and accurately controls the application of RF energy, within a specific thermal range, and delivers thermal energy to collagen soft tissue of, for instance joints, thereby contracting and restricting the soft tissue elasticity and improving joint stability. When applied to the shoulder, there is capsular shrinkage of the gleno-humeral joint capsule of the shoulder and a consequent contracture of the volume, the interior circumference, of the shoulder capsule to correct for recurrent instability symptoms. The degree of capsular shrinkage is determined by the operating surgeon, based on severity of preoperative symptoms and condition of the capsule at the time of arthroscopic inspection.

Figure 13:
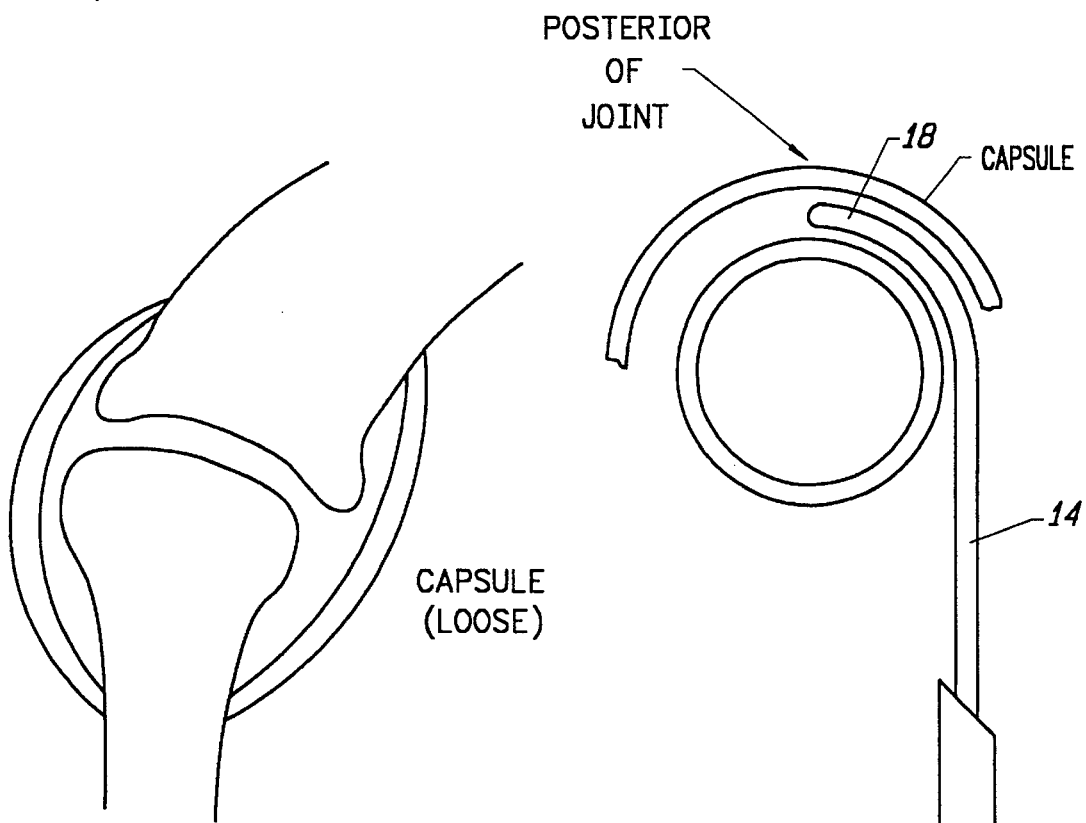
FIG. 13 is a cross-sectional diagram of a loose joint capsule.
Figure 14:
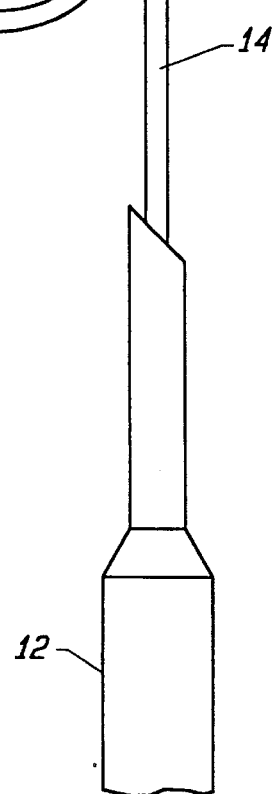
FIG. 14 is a cross-sectional diagram of the RF ablation device of the present invention and a joint capsule. The first RF electrode is moved along a surface of soft tissue and paints an ablation band.
Figures 15, 16:
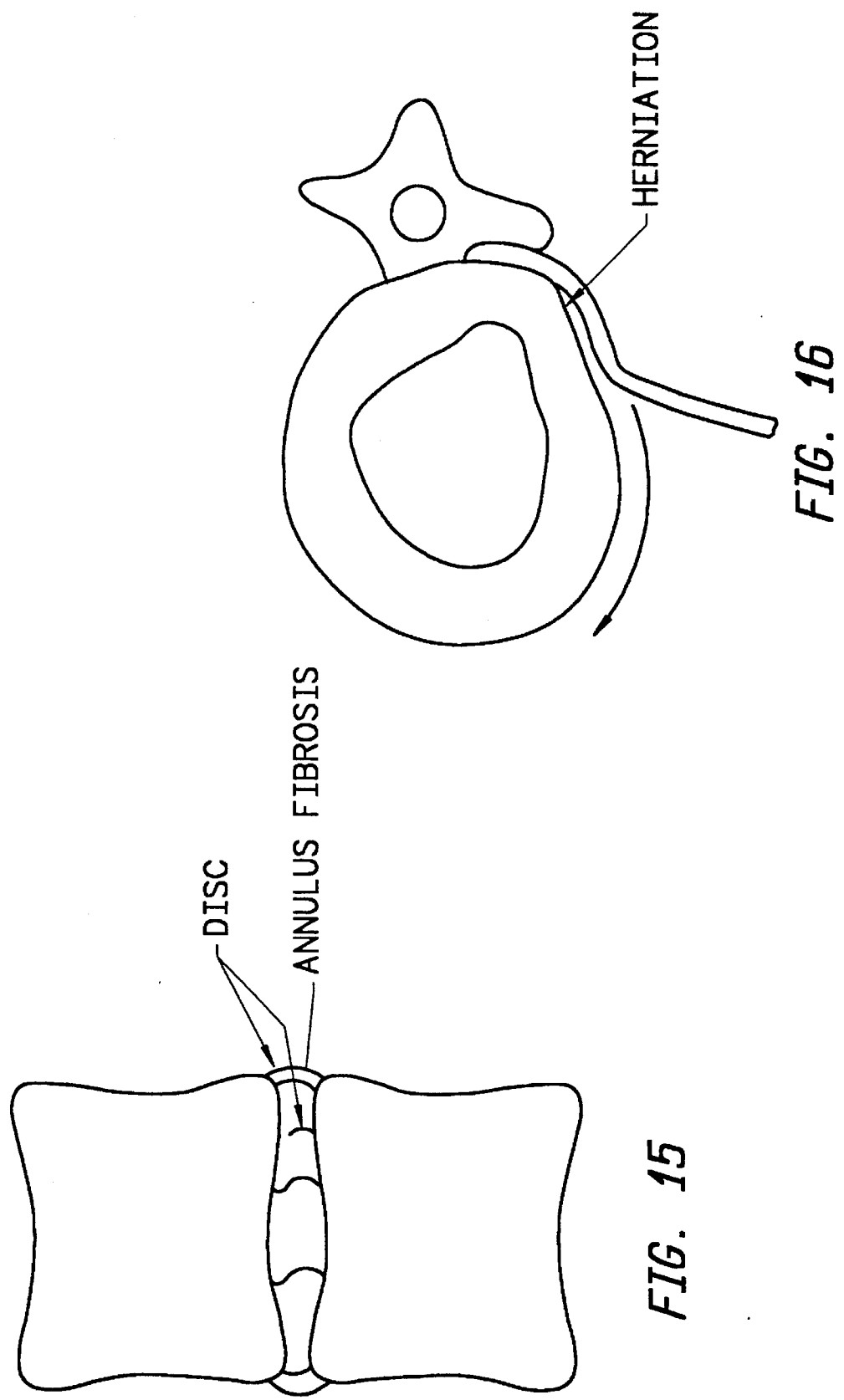
FIG. 15 is a cross-sectional diagram of a disc with annulus fibrosis.
FIG. 16 is a cross-sectional diagram of the RF ablation apparatus of the invention painting RF ablation energy along an ablation band.

In FIG. 13, a loose capsule is illustrated. Ablation apparatus 10 is applied to a joint capsule in FIG. 14. First and second RF electrodes 14 and 18 curve around the joint capsule to paint an ablation line of controlled depth, causing the desired level of shrinkage. Figures 15 and 16 illustrate the application of ablation apparatus 10 to a herniated disc.

Referring again to FIG. 1, one or more impedance monitors 60 and thermal sensors 62 can be included with first RF electrode 14 or second RF electrode 18. Impedance monitors 60 can be used to confirm, before an ablation event, that good coupling of energy is achieved. Thermal sensors 62 are of conventional design, including but not limited to thermistors, thermocouples, resistive wires, and the like.

Figure 17:
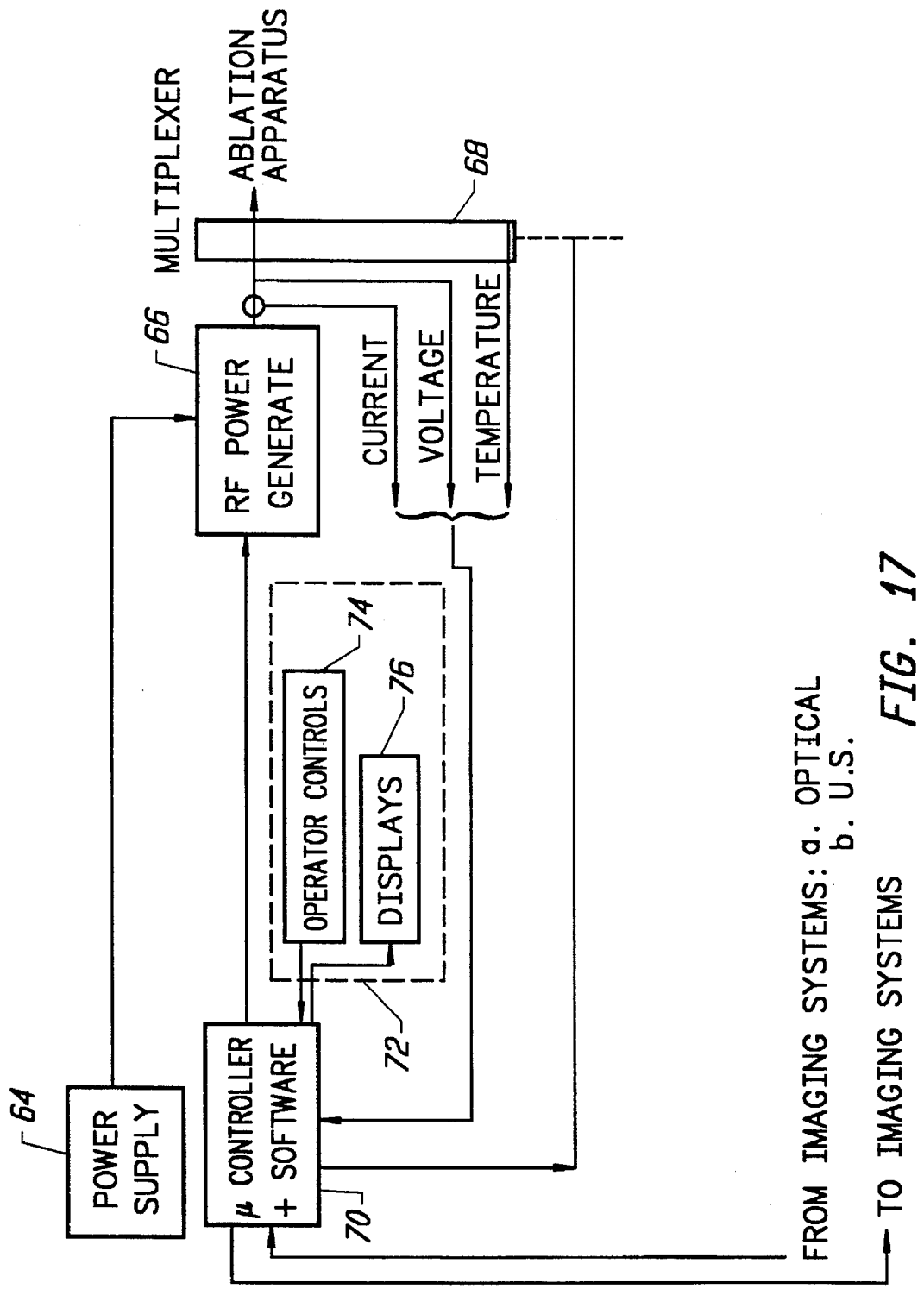
FIG. 17 is a block diagram of a feedback device which can be associated With the RF ablation apparatus.

As illustrated in FIG. 17, a power supply 64 feeds energy into RF power generator (source) 66 and then to ablation apparatus 10. A multiplexer 68 can be included to measure current, voltage and temperature. Multiplexer 68 is driven by a controller 70, which is a digital or analog, or a computer with software. When controller 70 is a computer, it can include a CPU coupled through a system bus. This system can include a keyboard, a disk drive, or other non-volatile memory systems, a display, and other peripherals, as well known in the art. Also coupled to the bus are a program memory and a data memory.

An operator interface 72 includes operator controls 74 and a display 76. Controller 70 can be coupled to various imaging systems, transducers 60, thermal sensors 62, as well as viewing optics and fibers.

Current and voltage are used to calculate impedance. An operator set level of power and/or temperature may be determined, and this will not be exceeded if desired. Controller 70 maintains the set level under changing conditions. The amount of RF energy delivered controls the amount of power. A profile of power deliver can be incorporated in controller 70, as well as a pre-set amount of energy to be delivered.

Feedback can be the measurement of impedance or temperature and occurs either at controller 70 or at RF source 66 if it incorporates a controller. Impedance measurement can be achieved by supplying a small amount of non-therapeutic RF energy. Voltage and current are then measured to confirm electrical contact.

Circuitry, software and feedback to controller 70 result in full process control and are used to change, (i) power (modulate) including RF, incoherent light, microwave, ultrasound and the like, (ii) the duty cycle (on-off and wattage), (iii) monopolar or bipolar energy delivery, (iv) fluid (electrolytic solution delivery, flow rate and pressure and (v) determine when ablation is completed through time, temperature and/or impedance.

Figure 18:
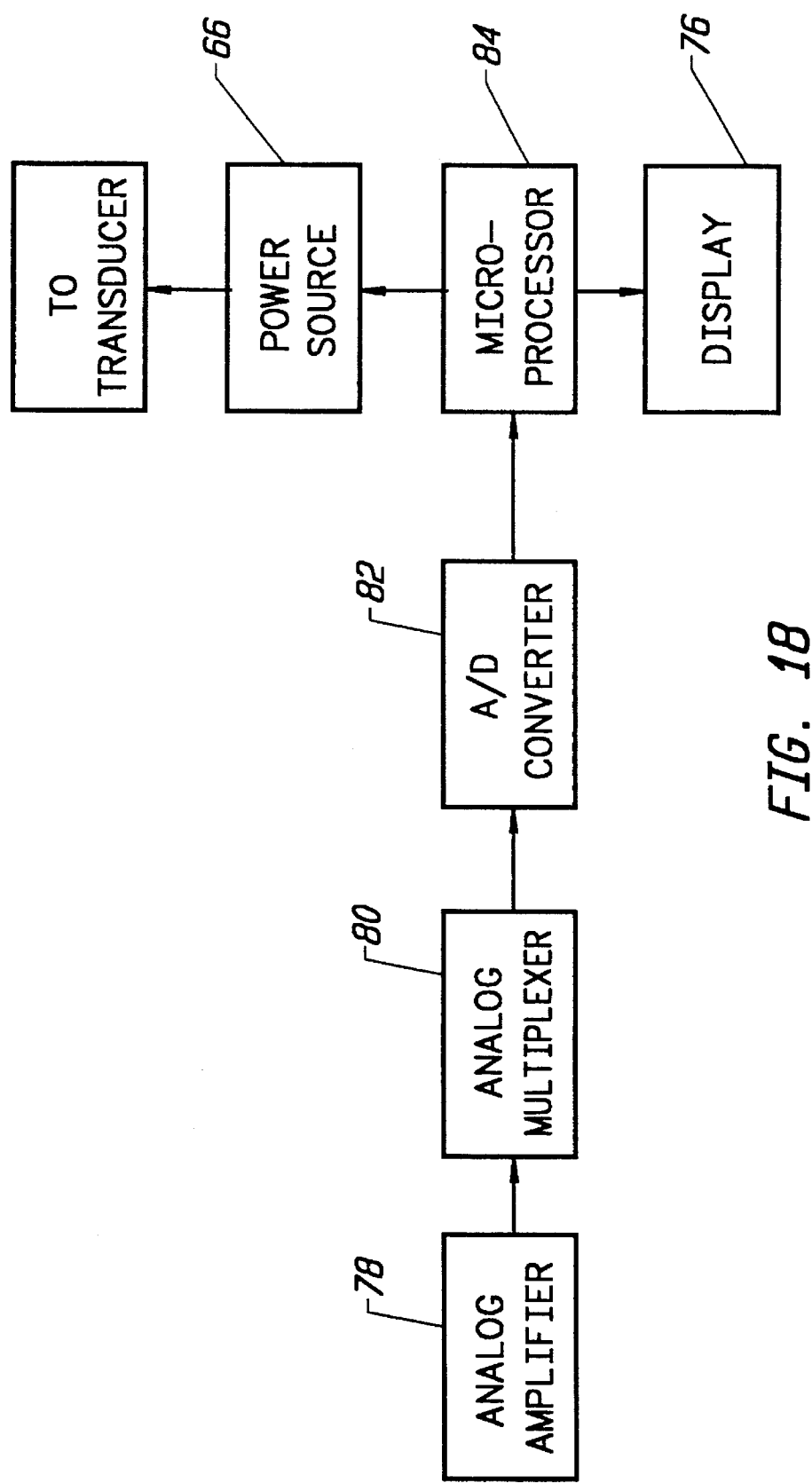
FIG. 18 is a circuitry block diagram of a feedback device of the present invention with a microprocessor.

A block diagram of one embodiment of suitable processing circuitry is shown in FIG. 18. Thermal sensors 62 and transducers 60 are connected to the input of an analog amplifier 78. Analog amplifier 78 can be a conventional differential amplifier circuit for use with thermistors and transducers. The output of analog amplifier is sequentially connected by an analog multiplexer 80. Analog amplifier 80 can be a conventional differential amplifier circuit for use with thermistors and transducers. The output of analog amplifier 78 is sequentially connected by an analog multiplexer 80 to the input of an analog to digital converter 82. The output of amplifier 78 is a voltage which represents the respective sensed temperatures. Digitized amplifier output voltages are supplied by analog to digital converter 82 to a microprocessor 84. Microprocessor 84 calculates the temperature or impedance of the tissue. Microprocessor 84 can be a type 68HCll. However, it will be appreciated that any suitable microprocessor or general purpose digital or analog computer can be used to calculate impedance or temperature.

Calculated temperature and impedance values can be indicated on display 76. Alternatively, or in addition to the numerical indication of temperature of impedance, calculated impedance and temperature values can be compared by microprocessor 84 with temperature and impedance limits. When the values exceed predetermined temperature or impedance values, a warning can be given on display 76. A control signal from microprocessor 84 can reduce the power level supplied by RF energy source 66, or deenergize the power delivered.

Thus, controller 70 receives and stores the digital values which represent temperatures and impedances sensed. Calculated surface temperatures and impedances can be forwarded by controller 70 to display 76.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications, as are suited to the particular use contemplated. It is intended that the scope of the invention be defined by the following claims and their equivalents.

What is claimed is:

1. An RF ablation apparatus, comprising:

a delivery catheter with a delivery catheter lumen and a delivery catheter distal end;

a first RF electrode positioned in the delivery catheter lumen, the first RF electrode having a first RF electrode distal end, a first RF electrode conductive surface, and a first RF electrode lumen;

a second RF electrode with a second RF electrode distal end and a second RF electrode conductive surface, the second RF electrode being at least partially positioned in the first RF electrode lumen with the second RF electrode distal end positioned at the exterior of the first RF electrode distal end, the first RF electrode being movable in a direction away from the second electrode distal end creating an ablation between the second RF electrode distal end and the first RF electrode distal end;

an RF insulative sleeve positioned along a selected section of the second RF electrode conductive surface; and an RF power source coupled to the first and second RF electrodes.

2. An RF ablation apparatus, comprising:
- a delivery catheter with a delivery catheter lumen and a delivery catheter distal end;
- a first RF electrode positioned in the delivery catheter lumen, the first RF electrode having a first RF electrode distal end, a first RF electrode conductive surface, and a first RF electrode lumen;
- a second RF electrode with a second RF electrode distal end and a second RF electrode conductive surface, the second RF electrode being at least partially positioned in the first RF electrode lumen with the second RF electrode distal end positioned at the exterior of the first RF electrode distal end, the second RF electrode distal end having a geometry that permits it to be substantially a groundpad, the first RF electrode being movable in a direction away from the second RF electrode distal end creating an ablation between the second RF electrode distal end and the first RF electrode distal end;
- an RF insulative sleeve positioned along a selected section of the second RF electrode conductive surface; and
- an RF power source coupled to the first and second RF electrodes.

3. The RF ablation apparatus of claim 1, wherein the RF insulative sleeve is positioned along the second RF electrode conductive surface, and the second RF electrode conductive surface is substantially adjacent to the first electrode conductive surface.

4. The RF ablation apparatus of claim 2, wherein the distal end of the second electrode is radiused.

5. The RF ablation apparatus of claim 2, wherein the distal end of the second electrode has radiused edges.

6. The RF ablation apparatus of claim 2, wherein at least a portion of the first electrode distal end has a sharp edge.

7. The RF ablation apparatus of claim 2, wherein the first electrode distal end has a non-radiused edge.

8. The RF ablation apparatus of claim 2, further comprising:
- a pull wire attached to the first electrode.

9. The RF ablation apparatus of claim 2, further comprising:
- a pull wire attached to the second electrode.

10. The RF ablation apparatus of claim 2 wherein the first electrode distal end is deployed laterally in relation to the distal end of the delivery catheter.

11. The RF ablation apparatus of claim 2, wherein the first electrode distal end is made of a memory metal.

12. The RF ablation apparatus of claim 2, wherein the second electrode distal end is deployed laterally in relation to the distal end of the delivery catheter.

13. The RF ablation apparatus of claim 2, wherein the second electrode distal end is made of a memory metal.

14. The RF ablation apparatus of claim 2, wherein the first electrode is slidably movable along the lumen of the delivery catheter.

15. The RF ablation apparatus of claim 2, wherein the first electrode is fixably positioned with the delivery catheter and movable with movement of the delivery catheter.

16. The RF ablation apparatus of claim 2 wherein the first electrode is partially RF insulated.

17. The RF ablation apparatus of claim 2, wherein at least a portion of the first electrode distal end is RF insulated.

18. The RF ablation apparatus of claim 2, wherein at least a portion of the second electrode distal end is RF insulated.

19. The RF ablation apparatus of claim 2, wherein the first electrode is fixed in relation to the delivery catheter.

20. The RF ablation apparatus of claim 2, wherein the first electrode is articulated in relation to the delivery catheter.

21. The RF ablation apparatus of claim 2, wherein the second electrode is fixed in relation to the delivery catheter.

22. The RF ablation apparatus of claim 2, wherein the second electrode is articulated in relation to the delivery catheter.

23. An RF ablation apparatus, comprising:
- a delivery catheter with a delivery catheter lumen;
- a first RF electrode positioned in the delivery catheter lumen, the first RF electrode having a first RF electrode distal end with an RF conductive surface, and a first RF electrode lumen;
- a second RF electrode including an elongated body that terminates at a second RF electrode distal end with an average diameter larger than an average diameter of the elongated body, the second RF electrode being at least partially positioned in the first RF electrode lumen with the second RF electrode distal end positioned at the exterior of the first RF electrode distal end, the first RF electrode being capable of movement in a direction away from the second RF electrode distal end to create an ablation band between the distal end of the second RF electrode and the first RF electrode distal end; and
- an RF power source coupled to the first and second RF electrodes.

24. The RF ablation apparatus of claim 23, further comprising:
- an RF insulative sleeve positioned along the elongated body of the second RF electrode.

25. The RF ablation apparatus of claim 24, wherein at least a portion of the second electrode distal end is RF insulated.

26. The RF ablation apparatus of claim 23, wherein the distal end of the second RF electrode has a geometry and size making it substantially a groundpad.

27. The RF ablation apparatus of claim 23, wherein the second electrode distal end is radiused.

28. The RF ablation apparatus of claim 23, wherein the second electrode distal end has radiused edges.

29. The RF ablation apparatus of claim 23, wherein the first electrode distal end has a sharp edge.

30. The RF ablation apparatus of claim 23, wherein the RF conductive surface of the first electrode distal end has a sharp edge.

31. The RF ablation apparatus of claim 23, wherein the RF conductive surface of the first electrode distal end has a non-radiused edge.

32. The RF ablation apparatus of claim 23, further comprising:
- a pull wire attached to the first electrode.

33. The RF ablation apparatus of claim 23, wherein the first electrode distal end is deployed laterally in relation to a longitudinal axis of the delivery catheter.

34. The RF ablation apparatus of claim 23, wherein the first electrode distal end is made of a memory metal.

35. The RF ablation apparatus of claim 23, wherein the second electrode distal end is deployed laterally in relation to a longitudinal axis of the delivery catheter.

36. The RF ablation apparatus of claim 23, wherein the second electrode distal end is made of a memory metal.

37. The RF ablation apparatus of claim 23, wherein the first electrode is slidably movable along the lumen of the delivery catheter.

38. The RF ablation apparatus of claim 23, wherein the first electrode is fixably positioned to the delivery catheter and movable with a movement of the delivery catheter.

39. The RF ablation apparatus of claim 23, wherein the first electrode is at least partially RF insulated.

40. The RF ablation apparatus of claim 23, wherein at least a portion of the first electrode distal end is RF insulated.

41. The RF ablation apparatus of claim 23, wherein at least a portion of the second electrode distal end is RF insulated.

42. The RF ablation apparatus of claim 23, further comprising:

a feedback device in response to a detected characteristic of the ablation band that provides a controlled delivery of RF energy to the first and second electrodes.

43. The ablation apparatus of claim 42, wherein the detected characteristic is an impedance at a section of the ablation band.

44. The ablation apparatus of claim 42, wherein the detected characteristic is a temperature profile at a section of the ablation band.

* * * * *